US005656413A

United States Patent [19]

Rahman et al.

[11] Patent Number: 5,656,413
[45] Date of Patent: Aug. 12, 1997

[54] LOW METAL ION CONTAINING 4,4'-[1-[4-[1-(4-HYDROXYPHENYL)-1-METHYLETHYL] PHENYL]ETHYLIDENE]BISPHE NOL AND PHOTORESIST COMPOSITIONS THEREFROM

[75] Inventors: M. Dalil Rahman, Flemington, N.J.; Daniel P. Aubin, Voluntown, Conn.

[73] Assignee: Hoechst Celanese Corporation, Somerville, N.J.

[21] Appl. No.: 535,701

[22] Filed: Sep. 28, 1995

[51] Int. Cl.$^6$ ............... G03C 5/56; C02F 1/42; H01L 21/312

[52] U.S. Cl. ............ 430/311; 430/168; 430/169; 430/325; 430/326; 430/330; 210/681; 210/683; 210/685; 438/948

[58] Field of Search ............ 430/168, 169, 430/325, 326, 330, 311; 210/681, 683, 685; 437/229

[56] References Cited

U.S. PATENT DOCUMENTS

| | | | |
|---|---|---|---|
| 2,929,808 | 4/1960 | Ross et al. | 260/94.9 |
| 4,033,909 | 7/1977 | Papa | 260/482 |
| 4,033,910 | 7/1977 | Papa | 260/25 F |
| 4,195,138 | 3/1980 | Ward | 525/404 |
| 4,250,031 | 2/1981 | Uejima et al. | 210/688 |
| 4,452,883 | 6/1984 | Frenchik et al. | 430/502 |
| 4,567,130 | 1/1986 | Held | 430/294 |
| 4,584,261 | 4/1986 | Held | 430/294 |
| 4,636,540 | 1/1987 | Warfel | 523/310 |
| 4,721,665 | 1/1988 | Dooley et al. | 430/270 X |
| 4,747,954 | 5/1988 | Vaughn et al. | 210/681 |
| 4,784,937 | 11/1988 | Tanaka et al. | 430/331 |
| 4,833,067 | 5/1989 | Tanaka et al. | 430/331 |
| 4,914,006 | 4/1990 | Kato et al. | 430/331 |
| 5,073,622 | 12/1991 | Wojtech et al. | 528/486 |
| 5,116,715 | 5/1992 | Roland | 430/190 |
| 5,118,787 | 6/1992 | Furuno | 528/482 |
| 5,175,078 | 12/1992 | Aoyama et al. | 430/331 |
| 5,212,044 | 5/1993 | Liang et al. | 430/270 X |
| 5,284,930 | 2/1994 | Matsumoto et al. | 528/482 |
| 5,286,606 | 2/1994 | Rahman et al. | 430/311 |
| 5,300,628 | 4/1994 | Honda | 528/482 |
| 5,350,714 | 9/1994 | Trefonas, III et al. | 210/663 X |
| 5,378,802 | 1/1995 | Honda | 210/660 X |
| 5,446,125 | 8/1995 | Honda et al. | 528/486 |
| 5,472,616 | 12/1995 | Szmanda et al. | 210/683 |
| 5,500,127 | 3/1996 | Carey et al. | 210/686 |
| 5,521,052 | 5/1996 | Rahman et al. | 430/270.1 |

FOREIGN PATENT DOCUMENTS

| | | |
|---|---|---|
| 435437 | 7/1991 | European Pat. Off. . |
| 544324 | 6/1993 | European Pat. Off. . |
| 544325 | 6/1993 | European Pat. Off. . |
| 0588492 | 3/1994 | European Pat. Off. . |
| 1072155 | 3/1989 | Japan . |
| 1-228560 | 9/1989 | Japan . |
| 4-65415 | 3/1992 | Japan . |
| 1509354 | 5/1978 | United Kingdom . |
| WO 90/01726 | 2/1990 | WIPO . |
| WO 93/12152 | 6/1993 | WIPO . |
| WO 93/18437 | 9/1993 | WIPO . |
| WO 94/01807 | 1/1994 | WIPO . |
| WO 94/12912 | 6/1994 | WIPO . |
| WO 94/14858 | 7/1994 | WIPO . |
| WO 94/14863 | 7/1994 | WIPO . |
| WO 96/12214 | 4/1996 | WIPO . |
| WO 96/20965 | 7/1996 | WIPO . |
| WO 96/21175 | 7/1996 | WIPO . |
| WO 96/21176 | 7/1996 | WIPO . |

OTHER PUBLICATIONS

Bayard; "Water Free of Heavy Metals for Medical Use and Ion Exchange Resin Used in its Preparation" Nov. 16, 1992; CA98(26):221589z.

Hirai et al; "Treatment of Waste Waters Containing Formaldehyde and Metals with Chelating Ion Exchange Resins"; Nov. 5, 1975; CA84(14):95328j.

Kimura et al; "Purification of Formaldehyde"; Mar. 9, 1977; CA87(7):52776y.

T. Tanada; "A New Photolithography Tech. with Antireflective ... "; Journal of the Electrochemical Society, vol. 137, No. 12, pp. 393900–393905; Dec. 1990, Manchester, New Hampshire.

Rohm and Haas Company; "Amberlite Ion Exchange Resins Laboratory Guide"; Sep. 1979; Philadelphia, PA.

JP-A-1190713 Inatomi, Shigeki et al, Jul. 31, 1989; Chemical Abstracts, vol. 112, No. 18, Apr. 30, 1990, Columbus, OH, p. 17, the Abstract 15920lu.

G. Noti et al, "Deionized Water Plants for Semiconductor Device Fabrication", Proceedings of the Inst:Radio and Electron. Eng, Aust.(Australia), vol. 34, No. 2, Mar. 1973, pp. 45–51.

JP 04036751 (Feb. 6, 1992).
JP 04177352 (Jun. 26, 1992).
JP 04298749 (Oct. 22, 1992).
JP 05019464 (Jan. 29, 1993).
JP 05163417 (Jun. 29, 1993).
Derwent, JP-A-05 234 876, OCG Microelectronic Materials, Sep. 10, 1993.

*Primary Examiner*—John S. Chu
*Attorney, Agent, or Firm*—Andrew F. Sayko, Jr.

[57] ABSTRACT

The present invention provides methods for producing TPPA having low level of metal ions, utilizing treated ion exchange resins. A method is also provided for producing photoresist composition having a very low level of metal ions from such TPPA for producing semiconductor devices using such photoresist compositions.

19 Claims, No Drawings

LOW METAL ION CONTAINING 4,4'-[1-[4-[1-(4-HYDROXYPHENYL)-1-METHYLETHYL]PHENYL]ETHYLIDENE]BISPHE NOL AND PHOTORESIST COMPOSITIONS THEREFROM

BACKGROUND OF THE INVENTION

The present invention relates to a process for producing low metal ion containing 4,4'-[1-[4-[1-(4-Hydroxyphenyl)-1 methylethyl]phenyl]ethylidene]bisphenol(TPPA), having a low level of metal ions, and for using such TPPA in light-sensitive photoresist compositions. The present invention also relates to a process for making light-sensitive compositions useful in positive-working photoresist compositions for lithography. Further, the present invention relates to a process for coating substrates with these light-sensitive compositions as well as the process of coating, imaging and developing these light-sensitive mixtures on substrates.

Photoresist compositions are used in microlithography processes for making miniaturized electronic components such as in the fabrication of computer chips and integrated circuits. Generally, in these processes, a thin coating of film of a photoresist composition is first applied to a substrate material, such as silicon wafers used for making integrated circuits. The coated substrate is then baked to evaporate any solvent in the photoresist composition and to fix the coating onto the substrate. The baked coated surface of the substrate is next subjected to an image-wise exposure to radiation.

This radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation-exposed or the unexposed areas of the coated surface of the substrate.

Metal contamination has been a problem for a long time in the fabrication of high density integrated circuits and computer chips, often leading to increased defects, yield losses, degradation and decreased performance. In plasma processes, metals such as sodium and iron, when they are present in photoresists, can cause contamination especially during plasma stripping. However, these problems have been overcome to a substantial extent during the fabrication process. For example, by utilizing HCL gettering of the contaminants during a high temperature anneal cycle.

As semiconductor devices have become more sophisticated, these problems have become much more difficult to overcome. When silicon wafers are coated with a liquid positive photoresist and subsequently stripped off, such as with oxygen microwave plasma, the performance and stability of the semiconductor device is often seen to decrease. As the plasma stripping process is repeated, more degradation of the device frequently occurs. A primary cause of such problems has been found to be the metal contamination in the photoresist, particularly sodium and iron ions. Metal levels of less than 1.0 ppm in the photoresist have been found to adversely affect the properties of such semiconductor devices.

Novolak resins are frequently used a polymeric binder in liquid photoresist formulations. These resins are typically produced by conducting a condensation reaction between formaldehyde or trioxane and one or more multi-substituted phenols, in the presence of an acid catalyst, such as oxalic acid.

There are two types of photoresist compositions, negative-working and positive-working. When negative-working photoresist compositions are exposed image-wise to radiation, the areas of the resist composition exposed to the radiation become less soluble to a developer solution (e.g. a cross-linking reaction occurs) while the unexposed areas of the photoresist coating remain relatively soluble to such a solution. Thus, treatment of an exposed negative-working resist with a developer causes removal of the non-exposed areas of the photoresist coating and the creation of a negative image in the coating. Thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the creation of a positive image in the photoresist coating. Again, a desired portion of the underlying substrate surface is uncovered.

After this development operation, now partially unprotected substrate may be treated with a substrate-etchant solution or plasma gases and the like. The etchant solution or plasma gases etch that portion of the substrate where the photoresist coating was removed during development. The areas of the substrate where the photoresist coating still remains are protected and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining photoresist layer, after the development step and before the etching step, to increase its adhesion to the underlying substrate and its resistance to etching solutions.

Positive working photoresist compositions are currently favored over negative working resists because the former generally have better resolution capabilities and pattern transfer characteristics. Photoresist resolution is defined as the smallest feature which the resist composition can transfer from the photomask to the substrate with a high degree of image edge acuity after exposure and development. In many manufacturing applications today, resist resolution on the order of less than one micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate.

DESCRIPTION OF THE PRIOR ART

A method of making a positive-working photosensitive resin composition for manufacturing semiconductor device using TPPA is disclosed in Japanese patents, JP 04036751 (2/6/92), JP 04177352 (6/24/92), JP 04298749 (10/22/92), JP 05019464 (1/29/93), JP 05163417 (6/29/93), all incorporated herein by reference.

SUMMARY OF THE INVENTION

The present invention relates to a process for producing TPPA containing low levels of metal ions, especially sodium and iron and a process for its use in photoresist compositions. The invention further relates to a process for making positive-working photoresists containing TPPA and a photosensitizer, and a process for using such photoresists in producing semiconductor devices.

TPPA, when purchased, typically has extremely high level of metal ions such as iron and sodium. Sodium and iron are the most common metal ion contaminants and among the easiest to detect. The level of these metal ions serves as an indicator of the level of other metal ions. After treating TPPA according to the process of the present invention, the level of sodium and iron ions is less than 200 ppb each, preferably less than 100 ppb each, more preferably less than 50 ppb each, even more preferably less than 30 ppb each, and most preferably less than 10 ppb each.

The present invention provides a process for producing TPPA having an extremely low level of metal ions. In one embodiment, the process utilizes an acidic ion exchange resin to purify the TPPA solution in a polar solvent or a mixture of polar solvents, such as methanol, ethanol, acetone or isopropanol, and in a particularly preferred embodiment, uses a cation exchange resin followed by purification of the same solution using an anion exchange resin. The subject process comprises:

a) washing an acidic ion exchange resin with deionized (DI) water, followed by washing with a mineral acid solution (e.g. a 5–98% solution of sulfuric, nitric or hydrochloric acid), followed by washing again with DI water, to thereby reduce the level of sodium and iron ions in the ion exchange resin to less than 200 ppb each, preferably less than 100 ppb each, more preferably less than 50 ppb each, even more preferably less than 30 ppb each, and most preferably less than 20 ppb each;

b) washing an anion exchange resin with DI water, followed by washing with a mineral acid solution (e.g. a 5–98% solution of sulfuric, nitric or hydrochloric acid) followed by washing again with DI water, then washing with an electronic grade ammonium hydroxide solution (4–28% solution in water), followed by washing with DI water again, to thereby reduce the level of sodium and iron ions in the anion exchange resin to less than 200 ppb each, preferably less than 100 ppb each, more preferably less than 50 ppb, even more preferably less than 30 ppb each and most preferably less than 20 ppb each;

c) making a slurry of TPPA in DI water about 1 to 20% solid, preferably 5 to 15% solid, more preferably 8 to 12% solid and filtering, e.g. through a Buckner funnel using Whiteman filter paper or through a bag filter, to provide a filter cake;

d) pouring the filter cake into DI water and again making a slurry about 1 to 20% solid, preferably 5 to 15% solid, more preferably 8 to 12% solid and filtering, through a filter;

e) making a solution of the filter cake of TPPA in a polar solvent, or a mixture of polar solvents, (5% to 35%, by weight, preferably 10% to 30% and most preferably 15% to 25% solids);

f) passing the TPPA solution through said cation exchange resin followed by passing said TPPA solution through said anion exchange resin and thereby reducing the level of metal ions in said TPPA solution to less than 100 ppb each, preferably less than 50 ppb, more preferably less than 25 ppb and most preferably less than 10 ppb;

g) adding the TPPA solution to DI water and thereby precipitating the TPPA;

h) filtering the TPPA through a filter, e.g. through a Buckner funnel using Whiteman filter paper or through a bag filter, and drying the TPPA, preferably in a vacuum oven.

The present invention further provides a process for producing a positive photoresist composition having a very low level of total sodium and iron ions. The subject process comprises:

a) washing an acidic ion exchange resin with deionized (DI) water, followed by washing with a mineral acid solution (e.g. a 5–98% solution of sulfuric, nitric or hydrochloric acid), followed by washing again with DI water, to thereby reduce the level of sodium and iron ions in the ion exchange resin to less than 200 ppb each, preferably less than 100 ppb each, more preferably less than 50 ppb each, even more preferably less than 30 ppb each, and most preferably less than 20 ppb each;

b) washing an anion exchange resin with DI water, followed by washing with a mineral acid solution (e.g. a 5–98% solution of sulfufic, nitric or hydrochloric acid) followed by washing again with DI water, then washing with an electronic grade ammonium hydroxide solution (4–28% solution in water), followed by washing with DI water again, to thereby reduce the level of sodium and iron ions in the anion exchange resin to less than 200 ppb each, preferably less than 100 ppb each, more preferably less than 50 ppb, even more preferably less than 30 ppb each and most preferably less than 20 ppb each;

c) making a slurry of TPPA in DI water about 1 to 20% solid, preferably 5 to 15% solid, more preferably 8 to 12% solid and filtering, e.g. through a Buckner funnel using Whiteman filter paper or through a bag filter, to provide a filter cake;

d) pouring the filter cake into DI water and again making a slurry about 1 to 20% solid, preferably 5 to 15% solid, more preferably 8 to 12% solid and filtering through a filter;

e) making a solution of the filter cake of TPPA in a polar solvent, or a mixture of polar solvents, (5% to 35%, by weight, preferably 10% to 30% and most preferably 15% to 25% solids);

f) passing the TPPA solution through said cation exchange resin followed by passing said TPPA solution through said anion exchange resin and thereby reducing the level of metal ions in said TPPA solution to less than 100 ppb each, preferably less than 50 ppb, more preferably less than 25 ppb and most preferably less than 10 ppb;

g) adding the TPPA solution to DI water and thereby precipitating the TPPA;

h) filtering the TPPA through a filter, e.g. through a Buckner funnel using Whiteman filter paper or through a bag filter, and drying the TPPA, preferably in a vacuum oven;

i) producing a photoresist composition by providing an admixture of: 1) a photosensitive component in an amount sufficient to photosensitize the photoresist composition; 2) a water insoluble, aqueous alkali soluble, film forming novolak resin having a very low level of metal ions 3) the purified TPPA and 4) a suitable photoresist solvent.

The invention further provides a method for producing a semiconductor device by producing a photo-image on a substrate by coating a suitable substrate with a positive working photoresist composition by:

a) washing an acidic ion exchange resin with deionized (DI) water, followed by washing with a mineral acid solution (e.g. a 5–98% solution of sulfuric, nitric or hydrochloric acid), followed by washing again with DI water, to thereby reduce the level of sodium and iron ions in the ion exchange resin to less than 200 ppb each, preferably less than 100 ppb each more preferably less than 50 ppb each, even more preferably less than 30 ppb each, and most preferably less than 20 ppb each;

b) washing an anion exchange resin with DI water, followed by washing with a mineral acid solution (e.g. a 5–98% solution of sulfuric, nitric or hydrochloric acid) followed by washing again with DI water, then washing with an electronic grade ammonium hydroxide solution (4–28% solution in water), followed by washing with DI water again, to thereby reduce the level of sodium and iron ions in the anion exchange resin to less than 200 ppb each, preferably less than 100 ppb each, more preferably less than 50 ppb, even more preferably less than 30 ppb each and most preferably less than 20 ppb each;

c) making a slurry of TPPA in DI water about 1 to 20% solid, preferably 5 to 15% solid, more preferably 8 to 12% solid and filtering, e.g. through a Buckner funnel using Whiteman filter paper or through a bag filter, to provide a filter cake;

d) pouring the filter cake into DI water and again making a slurry about 1 to 20% solid, preferably 5 to 15% solid, more preferably 8 to 12% solid and filtering through a filter;

e) making a solution of the filter cake of TPPA in a polar solvent, or a mixture of polar solvents, (5% to 35%, by weight, preferably 10% to 30% and most preferably 15% to 25% solids);

f) passing the TPPA solution through said cation exchange resin followed by passing said TPPA solution through said anion exchange resin and thereby reducing the level of metal ions in said TPPA solution to less than 100 ppb each, preferably less than 50 ppb, more preferably less than 25 ppb and most preferably less than 10 ppb;

g) adding the TPPA solution to DI water and thereby precipitating the TPPA;

h) filtering the TPPA through a filter, e.g. through a Buckner funnel using Whiteman filter paper or through a bag filter, and drying the TPPA, preferably in a vacuum oven;

i) producing a photoresist composition by providing an admixture of: 1) a photosensitive component in an amount sufficient to photosensitize the photoresist composition; 2) a water insoluble, aqueous alkali soluble, film forming novolak resin having a very low level of metal ions 3) the purified TPPA and 4) a suitable photoresist solvent;

j) coating a suitable substrate with the photoresist composition;

k) heat treating the coated substrate until substantially all of the solvent is removed; image-wise exposing the photoresist composition and removing the image-wise exposed areas of such composition with a suitable developer, such as an aqueous alkaline developer. Optionally one may perform a baking of the substrate either immediately before or after the removing step.

It has been found that TPPA having a very low level of metal ion contamination can not be obtained unless 1) it is washed with DI water, 2) it is mixed with a polar solvent, or a mixture of polar solvents, to provide a solution of 1% to 50% TPPA, preferably 5% to 40%, more preferably 10% to 30%, most preferably 15% to 25%; (2) passing it through an acidic ion exchange resin, such as Amberlyst®15 followed by passing it through an anion exchange resin, such as Amberlyst®21; and 3) passing through both ion exchange resins a solvent which is compatible with the solvent or solvents for the TPPA solution, prior to treating the TPPA solution with the ion exchange resins to remove metal ions.

DESCRIPTION OF THE PREFERRED EMBODIMENTS

An acidic ion exchange resin, such as a styrene/divinylbenzene cation exchange resin is utilized in the present process. Such ion exchange resins are available from Rohm and Haas Company, e.g. AMBERLYST®15 resin. These resins typically contain as much as 80,000 to 200,000 ppb of sodium and iron. Before being utilized in the process of the invention, the ion exchange resin must be treated with DI water and then a mineral acid solution to reduce the metal ion level. Preferably the ion exchange resin is initially rinsed with DI water, followed by a mineral acid solution such as a 10 percent sulfuric acid solution, rinsed again with DI water, treated again with the mineral acid solution and once again rinsed with DI water. Before purifying a TPPA solution, it is critical that the ion exchange resin is first rinsed with a solvent which is compatible with the TPPA solvent.

The TPPA solution is most preferably a methanol solution, contains 5–35 percent solids and is passed through columns containing the ion exchange resins. Such solutions typically contain from 750 to 150 ppb each of sodium and iron ions. During the process of the present invention, these levels are each reduced to as low as 10 ppb each.

The present invention provides a process for producing a photoresist composition and a process for producing semiconductor devices using such photoresist composition. The photoresist composition is formed by providing an admixture of a photosensitizer; a water insoluble, aqueous alkali soluble film forming novolak resin having a very low level of metal ions; TPPA, as an additive; and a suitable photoresist solvent. Suitable solvents for such photoresists and for novolak resin may include propylene glycol mono-alkyl ether, propylene glycol alkyl (e.g. methyl) ether acetate, ethyl-3-ethoxypropionate, ethyl lactate, 2-heptanone, mixtures of ethyl-3-ethoxypropionate and ethyl lactate, butyl acetate, xylene, diglyme, ethylene glycol monoethyl ether acetate. The preferred solvents are propylene glycol methyl ether acetate (PGMEA), ethyl lactate (EL) and ethyl-3-ethoxypropionate (EEP).

Other optional ingredients such as colorants, dyes, anti-striation agents, leveling agents, plasticizers, adhesion promoters, speed enhancers, solvents and such surfactants as non-ionic surfactants may be added to the solution of novolak resin, TPPA and photosensitizer, before the photoresist composition is coated onto a substrate. Examples of dye additives that may be used together with the photoresist compositions of the present invention include Methyl Violet 2B (C.I. No. 42535), Crystal Violet (C.I. 42555), Malachite Green (C.I. No. 42000), Victoria Blue B (C.I. No. 44045) and Neutral Red (C.I. No. 50040) at one to ten percent weight levels, based on the combined weight of PHS and sensitizer. The dye additives help provide increased resolution by inhibiting back scattering of light off the substrate.

Anti-striation agents may be used at up to about a five percent, by weight, level, based on the combined weight of novolak and sensitizer. Plasticizers which may be used include, for example, phosphoric acid tri-(beta-chioroethyl)-ester; stearic acid; dicamphor; polypropylene; acetal resins; phenoxy resins; and alkyl resins, at about one to ten percent weight levels, based on the combined weight of novolak and sensitizer. The plasticizer additives improve the coating properties of the material and enable the application of a film that is smooth and of uniform thickness to the substrate.

Adhesion promoters which may be used include, for example, beta-(3,4-epoxy-cyclohexyl)-ethyltrimethoxysilane; p-methyl-disilane-methyl methacrylate; vinyltrichlorosilane; and gamma-amino-propyl tri-ethoxysilane up to about a 4 percent weight level, based on the combined weight of novolak and sensitizer. Development speed enhancers that may be used include, for example, picric acid, nicotinic acid or nitrocinnamic acid up to about a 20 percent weight level, based on the combined weight of novolak and sensitizer. These enhancers tend to increase the solubility of the photoresist coating in both the exposed and unexposed areas, and thus they are used in applications when speed of development is the overriding consideration even though some degree of contrast may be sacrificed; i.e., while the exposed areas of the photoresist coating will be dissolved more quickly by the developer, the speed enhances will also cause a larger loss of photoresist coating from the unexposed areas.

The solvents may be present in the overall composition in an amount of up to 95% by weight of the solids in the composition. Solvents, of course are substantially removed after coating of the photoresist solution on a substrate and drying. Non-ionic surfactants that may be used include, for example, nonylphenoxy poly(ethyleneoxy) ethanol; octylphenoxy ethanol at up to about 10% weight levels, based on the combined weight of novolak and sensitizer.

The prepared photoresist solution, can be applied to a substrate by any conventional method used in the photoresist art, including dipping spraying, whirling and spin coating. When spin coating, for example, the resist solution can be adjusted with respect to the percentage of solids content, in order to provide coating of the desired thickness, given the type of spinning equipment utilized and the amount of time allowed for the spinning process. Suitable substrates include silicon, aluminum, polymeric resins, silicon dioxide, doped silicon dioxide, silicon nitride, tantalum, copper, polysilicon, ceramics, aluminum/copper mixtures; gallium arsenide and other such Group III/V compounds.

The photoresist coatings produced by the described procedure are particularly suitable for application to thermally grown silicon/silicon dioxide-coated wafers, such as are utilized in the production of microprocessors and other miniaturized integrated circuit components. An aluminum/aluminum oxide wafer can also be used. The substrate may also comprise various polymeric resins, especially transparent polymers such as polyesters. The substrate may have an adhesion promoted layer of a suitable composition, such as one containing hexa-alkyl disilazane.

The photoresist composition solution is then coated onto the substrate, and the substrate is treated at a temperature from about 70° C. to about 110° C. for from about 30 seconds to about 180 seconds on a hot plate or for from about 15 to about 90 minutes in a convection oven. This temperature treatment is selected in order to reduce the concentration of residual solvents in the photoresist, while not causing substantial thermal degradation of the photosensitizer. In general, one desires to minimize the concentration of solvents and this first temperature treatment is conducted until substantially all of the solvents have evaporated and a thin coating of photoresist composition, on the order of one micron in thickness, remains on the substrate. In a preferred embodiment the temperature is from about 85° C. to about 95° C. The treatment is conducted until the rate of change of solvent removal becomes relatively insignificant. The temperature and time selection depends on the photoresist properties desired by the user, as well as the equipment used and commercially desired coating times. The coating substrate can then be exposed to actinic radiation, e.g., ultraviolet radiation, at a wavelength of from about 300 nm to about 450 nm, x-ray, electron beam, ion beam or laser radiation, in any desired pattern, produced by use of suitable masks, negatives, stencils, templates, etc.

The photoresist is then optionally subjected to a post exposure second baking or heat treatment either before or after development. The heating temperatures may range from about 90° C. to about 120° C., more preferably from about 100° C to about 110° C. The heating may be conducted for from about 30 seconds to about 2 minutes, more preferably from about 60 seconds to about 90 seconds on a hot plate or about 30 to about 45 minutes by convection oven.

The exposed photoresist-coated substrates are developed to remove the image-wise exposed areas by immersion in an alkaline developing solution or developed by spray development process. The solution is preferably agitated, for example, by nitrogen burst agitation. The substrates are allowed to remain in the developer until all, or substantially all, of the photoresist coating has dissolved from the exposed areas. Developers may include aqueous solutions of ammonium or alkali metal hydroxides. One preferred hydroxide is tetramethyl ammonium hydroxide. After removal of the coated wafers from the developing solution, one may conduct an optional post-development heat treatment or bake to increase the coating's adhesion and chemical resistance to etching solutions and other substances. The post-development heat treatment can comprise the oven baking of the coating and substrate below the coating's softening point. In industrial applications, particularly in the manufacture of microcircuitry units on silicon/silicon dioxide-type substrates, the developed substrates may be treated with a buffered, hydrofluoric acid base etching solution. The photoresist compositions of the present invention are resistant to acid-base etching solutions and provide effective protection for the unexposed photoresist-coating areas of the substrate.

The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLE 1

110 grams of dry AMBERLYST®15 acidic ion exchange resin beads were placed in a conical flask and deionized water was added so that all of the resin beads were under water. The flask was sealed and allowed to stand overnight to swell the resin beads. The next morning the water was decanted, deionized water added to cover the resin beads and the flask was shaken slowly. The water was again decanted. The rinsing with deionized water and decanting steps were repeated three more times. The resulting slurry of acidic ion exchange resin was poured into a glass column equipped with a porous disk and a stopcock. The resin was allowed to settle to the bottom and the column was back flushed with deionized water for 25 minutes. The resin was again allowed to settle to the bottom.

The bed length was measured and the bed volume was calculated to be 200 ml. 6 bed volumes of a 10 weight percent sulfuric acid solution were passed down through the acidic ion exchange resin bed at a rate of about 20 ml./min. 60 bed volumes of deionized water were then passed down through the acidic ion exchange resin bed at about the same flow rate. The pH of the effluent water was measured to assure that it matched the pH of 6 for fresh deionized water. Two bed volumes of electronic grade methanol was passed down through the column.

160 grams of wet Amberlyst®21 anion exchange resin beads were placed in a conical flask and deionized water was added so that all of the resin beads were under water. The flask was sealed and allowed to stand overnight to swell the resin beads. The next morning the water was decanted, deionized water added to cover the anion exchange resin beads and the flask was shaken slowly. The water was again decanted. The rinsing with deionized water and decanting steps were repeated three more times. The resulting slurry of anion exchange resin was poured into a glass column having a diameter equipped with a porous disk and a stopcock. The anion exchange resin was allowed to settle to the bottom and the column was back flushed with deionized water for 25 minutes. The aion exchange resin was again allowed to settle to the bottom.

The bed length was measured and the bed volume was calculated as 260 ml. 6 bed volumes of a 10 percent sulfuric acid solution were passed down through the anion exchange resin bed at a rate of about 26 ml./min. A sufficient amount of deionized water were then passed down through the anion exchange resin bed at about the same flow rate, to remove the sulfuric acid. 6 bed volumes of an ammonium hydroxide solution (6% by weight volumes) were passed down through the column at the same rate, followed by about 60 bed volumes of DI water, to remove ammonium hydroxide. The pH of the effluent water was measured to assure that it matched the pH of 6 for fresh deionized water. 2 bed volumes of electronic grade methanol were then passed down through the column, to remove water, 1) DI water(1350 g) was placed in a 2 liter beaker and TPPA(150 g) was added, while stirring, to make a slurry. 2) After 30 minutes stirring, the slurry was filtered through a Buchner funnel and washed with DI water. Steps 1 & 2 were repeated twice. The resulting wet filter cake of TPPA (138 g) was dissolved, using electronic grade methanol (560 g), to a make TPPA solution in methanol (20%, by weight, solids). The TPPA/methanol solution was passed through a 0.1, μm (micrometer) filter and then through a precleaned Amberlyst®21 resin (as described above) column followed by a precleaned Amberlyst®15 resin (as described above) column with a residence time 10–12 minutes each and discharged to a clean container. Samples were taken before and after each column for metal ion analysis. Deionized TPPA solution was charged into a beaker and DI water was added slowly, while stirring, to provide a precipitate (8 parts DI water to 1 part TPPA solution). The precipitate was filtered through a clean Buckner funnel and then dried in a vacuum oven at 60° C. under 26 inches pressure (11–12 hours to dry, <0.5% water). The results of the metal ions analysis are shown in Table 1 below.

TABLE 1

| Metals | Control TPPA- Solid | Treated with Water, After Filtration (wet cake) | After A-21* (20% in methanol) | After A-15** (20% in methanol) | Solid TPPA |
|---|---|---|---|---|---|
| Na,ppb | >10,000 | 1880 | 750 | <5 | 22 |
| Fe,ppb | 688 | 465 | 100 | 7 | 32 |

*A-21: Amberlyst ® 21 ion exchange resin
**A-15: Amerlyst ® 15 ion exchange resin

EXAMPLE 2

Example #1 was repeated except the sequence of the ion exchange columns was changed. In this example the TPPA solution was first treated with A-15 resin, followed by A-21 resin. The results of the metal ion analysis are shown in Table 2 below.

TABLE 2

| Metals | Control TPPA- Solid | Treated with Water, After Filtration (wet cake) | After A-15 (20% in methanol) | After A-21 (20% in methanol) | Solid TPPA |
|---|---|---|---|---|---|
| Na, ppb | >10,000 | 1880 | <5 | <5 | 18 |
| Fe, ppb | 688 | 465 | 29 | 9 | 35 |

COMPARATIVE EXAMPLE 3

Example 1 was repeated without the DI water wash. It was not effective for removing sodium as shown below in Table 3.

TABLE 3

| Metals | Control Solid | Control (solution) | Filter | A-21 | A-15 | Solid |
|---|---|---|---|---|---|---|
| Na, ppb | >1000 | >1000 | >1000 | >1000 | >1000 | >1000 |
| Fe, ppb | >1000 | 109 | 67 | <5 | <5 | 40 |

COMPARATIVE EXAMPLE 4

A 50 gram photoresist test sample was prepared according to the following formulation:

1703L Novolak Resin (m-cresol/p-cresol/trioxane fractionated novolak resin (available from the AZ Photoresist Products Division of Hoechst Celanese Corp.)= 58.8% on the basis of total solids.

4382H Novolak Resin (m-cresol/p-cresol/formaldehyde fractionated novolak resin (available from the AZ Photoresist Products Division of Hoechst Celanese Corp.) =21% on the basis of total solids.

TPPA from Example 1=4.2%.

Diazonapthoquninone ester of trihydroxyphenylethane (60/40 of 2,1,5 or 2,1,4-)=4.0%.

RI-1186 (2,1,4- or 2,1,5- diazonapthoquinone ester of 2,3,4- tetra hydroxy phenyl benzophenone, 99% ester= 12%.

The resist sample was coated on an HMDS (hexamethyldisilazane) primed silicon wafer to a 1.18 μm (micrometer) thickness and the wafers were soft baked at 90° C. for 60 seconds on an I-line hot plate (SVG® 8100). The exposure matrix was printed on both coated wafers using a 0.54 NA NIKON® i-line stepper and a NIKONφ resolution reticle. The exposed wafers were post exposure baked (PEB) at 110° C. for 60 seconds on an SVG® 8100 I-line hot plate. The wafers were then developed using AZ®300 MIF/TMAH developer. The developed wafers were examined using a HITACHI®S-400 scanning electron microscope (SEM). A nominal dose (Dose to Print-DTP) was measured at the best focus, the dose required to precisely replicate a given feature. DTP, resolution, and depth of focus were measured and are shown below in Table 5.

TABLE 5

| | |
|---|---|
| DTP= | 130 mj/cm$^2$ |
| Resolution= | 0.36 μm (micrometer) |
| Depth of focus= | 0.6/0.6 μm (micrometer) |

We claim:

1. A method for producing a low metal ion containing TPPA comprising:
   a) washing an acidic ion exchange resin with deionized water, followed by washing with a mineral acid solution, followed by washing again with deionized water, and thereby reducing the level of sodium and iron ions in the acidic ion exchange resin to less than 200 ppb each;
   b) washing an anion exchange resin with deionized water, followed by washing with a mineral acid solution followed by washing again with deionized water, then washing with an ammonium hydroxide solution, followed by washing with deionized water again, and thereby reducing the level of sodium and iron ions in the anion exchange resin to less than 200 ppb each;
   c) making a slurry of TPPA in deionized water of about 1 to 20% solid, and filtering to provide a filter cake;
   d) pouring the filter cake into deionized water and again making a slurry of about 1 to 20% solid, and filtering;
   e) making a solution of the filter cake of TPPA in a polar solvent, or a mixture of polar solvents;
   f) passing the TPPA solution through said acidic ion exchange resin followed by passing said TPPA solution through said anion exchange resin and thereby reducing the level of metal ions in said TPPA solution to less than 100 ppb each;
   g) adding the TPPA solution to deionized water and thereby precipitating the TPPA;
   h) filtering the TPPA through a filter, and drying the TPPA.

2. The method of claim 1 wherein said anion exchange resin and said acidic ion exchange resin are each washed to reduce the sodium and iron ion level to less than 100 ppb each.

3. The method of claim 1 wherein said solution polar solvent is one or more of methanol, ethanol, acetone or isopropanol.

4. The method of claim I wherein the resulting TPPA solution has a sodium and iron ion level of less than 50 ppb each.

5. The method of claim 1 wherein the resulting TPPA solution in polar solvent has a sodium and iron ion level of less than 25 ppb each.

6. The method of claim 1 wherein the resulting TPPA solid after drying has a sodium and iron ion level of less than 10 ppb each.

7. A method for producing a positive photoresist composition comprising:
   a) washing an acidic ion exchange resin with deionized water, followed by washing with a mineral acid solution, followed by washing again with deionized water, and thereby reducing the level of sodium and iron ions in the acidic ion exchange resin to less than 200 ppb each;
   b) washing an anion exchange resin with deionized water, followed by washing with a mineral acid solution followed by washing again with deionized water, then washing with an ammonium hydroxide solution, followed by washing with deionized water again, and thereby reducing the level of sodium and iron ions in the anion exchange resin to less than 200 ppb each;
   c) making a slurry of TPPA in deionized water of about 1 to 20% solid, and filtering to provide a filter cake;
   d) pouring the filter cake into deionized water and again making a slurry of about 1 to 20% solid, and filtering;
   e) making a solution of the filter cake of TPPA in a polar solvent, or a mixture of polar solvents;
   f) passing the TPPA solution through said acidic ion exchange resin followed by passing said TPPA solution through said anion exchange resin and thereby reducing the level of metal ions in said TPPA solution to less than 100 ppb each;
   g) adding the TPPA solution to deionized water and thereby precipitating the TPPA;
   h) filtering the TPPA through a filter, and drying the TPPA;
   i) producing a photoresist composition by providing an admixture of: 1) a photosensitive component in an amount sufficient to photosensitize the photoresist composition; 2) a water insoluble, aqueous alkali soluble, film forming novolak resin 3) the purified TPPA and 4) a suitable photoresist solvent.

8. The method of claim 7 wherein said anion ion exchange resin and said acidic ion exchange resin are each washed to reduce the sodium and iron ion level to less than 100 ppb each.

9. The method of claim 7 wherein said solution polar solvent is one or more of methanol, ethanol, acetone or isopropanol.

10. The method of claim 7 wherein the TPPA solution has a sodium and iron ion level of less than 50 ppb each.

11. The method claim 8 wherein the TPPA solution in polar solvent has a sodium and iron ion level of less than 25 ppb each.

12. The method of claim 7 wherein said photoresist solvent is selected from the group consisting of propylene glycol methyl ether acetate, ethyl lactate and ethyl-3-ethoxypropionate.

13. A method for producing a semiconductor device by producing a photo-image on a suitable substrate comprising:
   a) washing an acidic ion exchange resin with deionized water, followed by washing with a mineral acid solution, followed by washing again with deionized water, and thereby reducing the level of sodium and iron ions in the acidic ion exchange resin to less than 200 ppb each;
   b) washing an anion exchange resin with deionized water, followed by washing with a mineral acid solution followed by washing again with deionized water, then washing with an ammonium hydroxide solution, followed by washing with deionized water again, and thereby reducing the level of sodium and iron ions in the anion exchange resin to less than 200 ppb each;
   c) making a slurry of TPPA in deionized water of about 1 to 20% solid, and filtering to provide a filter cake;

d) pouring the filter cake into deionized water and again making a slurry of about 1 to 20% solid, and filtering;

e) making a solution of the filter cake of TPPA in a polar solvent, or a mixture of polar solvents;

f) passing the TPPA solution through said acidic ion exchange resin followed by passing said TPPA solution through said anion exchange resin and thereby reducing the level of metal ions in said TPPA solution to less than 100 ppb each;

g) adding the TPPA solution to deionized water and thereby precipitating the TPPA;

h) filtering the TPPA through a filter, and drying the TPPA;

i) producing a photoresist composition by providing an admixture of 1) a photosensitive component in an amount sufficient to photosensitize the photoresist composition; 2) a water insoluble, aqueous alkali soluble, film forming novolak resin having a very low level of metal ions 3) the purified TPPA and 4) a suitable photoresist solvent;

j) coating a suitable substrate with the photoresist composition;

k) heat treating the coated substrate until substantially all of the solvent is removed; image-wise exposing the photoresist composition and removing the image-wise exposed areas of such composition with a suitable developer, as an aqueous alkaline developer; optionally one may perform a baking of the substrate either immediately before or after the removing step.

14. The method of claim 13 wherein said ion exchange resin is washed to reduce the total sodium and iron ion level to less than 100 ppb.

15. The method of claim 13 wherein said solution polar solvent is one or more of methanol, ethanol, acetone or isopropanol.

16. The method of claim 13 wherein the TPPA solution has a sodium and iron ion level of less than 100 ppb each.

17. The method claim 13 wherein the TPPA solution in polar solvent has a sodium and iron ion level of less than 20 ppb each.

18. The method claim 13 wherein the TPPA solid after drying in a vacuum has a sodium and iron ion level of less than 60 ppb each.

19. The method of claim 13 wherein said solvent is selected from the group consisting of propylene glycol methyl ether acetate, ethyl lactate and ethyl-3-ethoxypropionate.

* * * * *